(12) United States Patent  (10) Patent No.: US 9,188,567 B2
MacLauchlan et al.  (45) Date of Patent: *Nov. 17, 2015

(54) ULTRASONIC INSPECTION METHOD

(75) Inventors: Daniel T. MacLauchlan, Lynchburg, VA (US); Bradley E. Cox, Forest, VA (US)

(73) Assignee: BWXT Technical Services Group, Inc., Lynchburg, VA (US)

( * ) Notice: Subject to any disclaimer, the term of this patent is extended or adjusted under 35 U.S.C. 154(b) by 755 days.

This patent is subject to a terminal disclaimer.

(21) Appl. No.: 12/916,748

(22) Filed: Nov. 1, 2010

(65) Prior Publication Data

US 2011/0120223 A1 May 26, 2011

Related U.S. Application Data

(62) Division of application No. 11/564,346, filed on Nov. 29, 2006, now Pat. No. 7,823,454.

(51) Int. Cl.
*G01N 29/04* (2006.01)
*G01N 29/28* (2006.01)
(Continued)

(52) U.S. Cl.
CPC ............. *G01N 29/28* (2013.01); *G01N 29/265* (2013.01); *G01N 29/44* (2013.01); *G01N 29/4463* (2013.01); *G01N 2291/106* (2013.01)

(58) Field of Classification Search
CPC .................................................. G01N 29/4463
USPC .......................................................... 73/618
See application file for complete search history.

(56) References Cited

U.S. PATENT DOCUMENTS 4,010,635 A   3/1977  Patsey
4,252,022 A   2/1981  Hurwitz
(Continued)

FOREIGN PATENT DOCUMENTS

GB        2285129 A     6/1995
JP      2005-241611 A   9/2005
(Continued)

OTHER PUBLICATIONS

O. Casula et al.; "A Flexible Phased Array Transducer for Contact Examination of Components with Complex Geometry;" presented at the 16th World Conference on Nondestructive Testing in Montreal, Canada Aug. 30 to Sep. 3, 2004.
(Continued)

*Primary Examiner* — John Chapman, Jr.
(74) *Attorney, Agent, or Firm* — Nelson Mullins Riley & Scarborough, LLP

(57) ABSTRACT

A method for ultrasonically inspecting components with wavy or uneven surfaces. A multi-element array ultrasonic transducer is operated with a substantial fluid layer, such as water, between the array transducer and the component surface. This fluid layer may be maintained by immersing the component in liquid or by using a captive couplant column between the probe and the component surface. The component is scanned, measuring the two dimensional surface profile using either a mechanical stylus, laser, or ultrasonic technique. Once an accurate surface profile of the component's surface has been obtained, data processing parameters are calculated for processing the ultrasonic signals reflected from the interior of the component that eliminate beam distortion effects and reflector mis-location that would otherwise occur due to the uneven surfaces.

14 Claims, 4 Drawing Sheets

(51) Int. Cl.
*G01N 29/44* (2006.01)
*G01N 29/265* (2006.01)

(56) References Cited

U.S. PATENT DOCUMENTS

| | | | |
|---|---|---|---|
| 4,631,965 | A | 12/1986 | De Vadder et al. |
| 5,024,094 | A | 6/1991 | Kubota et al. |
| 5,275,052 | A * | 1/1994 | Luttrell et al. .................. 73/619 |
| 5,549,002 | A | 8/1996 | Howard et al. |
| 6,343,510 | B1 | 2/2002 | Neeson et al. |
| 6,424,597 | B1 | 7/2002 | Bolomey et al. |
| 6,877,376 | B1 | 4/2005 | Schuster et al. |
| 7,194,908 | B2 | 3/2007 | Nenno et al. |
| 7,594,439 | B2 | 9/2009 | Fischer et al. |
| 2005/0150300 | A1 | 7/2005 | Nenno et al. |
| 2005/0276466 | A1 * | 12/2005 | Vaccaro et al. ............... 382/152 |

FOREIGN PATENT DOCUMENTS

| | | | |
|---|---|---|---|
| JP | 3766210 | B2 | 4/2006 |
| JP | 2006-138672 | A | 6/2006 |

OTHER PUBLICATIONS

C. Holmes et al.; "The Post-Processing of Ultrasonic Array Data Using the Total Focusing Method;" Insight; vol. 46; No. 11; pp. 677 to 680 (2004).

O. Casula et al.; Control of Complex Components with Smart Flexible Phase Arrays; Ultrasonics, vol. 44, pp. e647 to e651, 2006.

P. D. Wilcox et al.; Exploiting the Full Data Set from Ultrasonic Arrays by Post-Processing; AIP Conference Proceedings, vol. 820, pp. 845 to 852, 2005.

Extended European Search Report dated Aug. 20, 2013 for corresponding European Patent Application No. 13170219.3.
Office Action dated Jul. 30, 2009 for Canadian Patent Application No. 2,608,483.
Second Office Action dated Apr. 12, 2010 for Canadian Patent Application No. 2,608,483.
Office Action dated Jan. 22, 2010 for Chinese Patent Application No. 200710196418.4.
Second Office Action dated Sep. 1, 2010 for Chinese Patent Application No. 200710196418.4.
Third Office Action dated May 31, 2011 for Chinese Patent Application No. 200710196418.4.
Fourth Office Action dated Mar. 21, 2012 for Chinese Patent Application No. 200710196418.4.
Office Action dated Jun. 11, 2010 for European Patent Application No. 07254351.5.
Office Action dated Oct. 20, 2010 for European Patent Application No. 07254351.5.
Office Action dated Apr. 23, 2014 for European Patent Application No. 13170219.3.
Office Action dated Oct. 14, 2010 for Japanese Patent Application No. 2007-300420.
Second Office Action dated Aug. 22, 2011 for Japanese Patent Application No. 2007-300420.
Third Office Action dated Sep. 13, 2012 for Japanese Patent Application No. 2007-300420.
Fourth Office Action dated Sep. 2, 2013 for Japanese Patent Application No. 2007-300420.
Office Action dated Sep. 6, 2010 for Korean Patent Application No. 2007-119117.
Second Office Action dated Sep. 29, 2011 for Korean Patent Application No. 2007-119117.

* cited by examiner

ULTRASONIC INSPECTION METHOD

RELATED APPLICATION DATA

This application claims priority to and is a divisional of U.S. patent application Ser. No. 11/564,346, filed Nov. 29, 2006, which issued as U.S. Pat. No. 7,823,454, the entirety of which is hereby incorporated herein by reference.

FIELD AND BACKGROUND OF INVENTION

The invention is generally related to inspection of component parts and, more particularly, to the ultrasonic inspection of component parts.

Components with complex shaped surfaces are common throughout industrial and government operation. Many times, the precise shape of these surfaces is not known prior to the need to perform an inspection. For example, in the commercial nuclear reactor industry there are many complex curved components and welds. Currently available qualified methods and procedures for performing ultrasonic (UT) examination of pipe welds from the outside surface are applicable only to geometries that are essentially flat and smooth. Field experience gained to date with these procedures shows that a significant portion of these welds are neither flat nor smooth. Typical field conditions encountered by UT examiners include variations in weld crown conditions and a range of other surface irregularities such as diametrical weld shrinkage.

Phased array ultrasonic testing of industrial components has gained widespread use in the past two decades. Phased array ultrasonic testing is a form of ultrasonic testing in which the transducer is comprised of an array of small individual elements, each with their own pulser and receiver channel. Each element is small so as to insure wide beam spread. On transmission, each element is pulsed at a precisely determined time so that the ultrasonic wave from each element arrives at the same time at a focal point in the components volume. On reception, the signal from each element is delayed by a precise time so that the signals reflected from the focal point in the component's volume will all be in phase. The delayed received signals are then summed together, producing a maximum amplitude signal when the reflection originates from the focal point. Since these time delays for transmission and reflection are electronically applied, they can be rapidly changed. This allows the phased array beam characteristics to be programmed and changed rapidly, at rates as high as 20,000 times per second. Using these techniques, the ultrasonic beam's focal point can be electronically swept in angle, swept through a range in depth, swept linearly along parallel to the probe, or any other desired pattern. This versatility has led to wide spread use of phased array ultrasonics in industrial testing.

Components with curved, wavy, or irregular surfaces have long been a challenge for ultrasonic testing. If the surface has a known regular geometry (such as a cylinder), in some cases an ultrasonic probe can be designed and fabricated to allow the component to be inspected. Using phased array ultrasonics, it is possible to compensate (in many cases) for known surface geometries by adjusting the delay times used in transmission and reception. Focal law calculators are commercially available that allow phased array ultrasonic beams to be designed for simple regular surface geometries. However, when the surface profile varies in unknown ways along the surface prior to inspection, no method has been available to perform ultrasonic inspection. This may occur, for example, when a pipe has been welded and then the weld ground to a smooth finish but not flat. Oftentimes a water path is used between the transducer and the part to conduct the ultrasonic waves into and out of the part, making it easier to perform automated scanning and to obtain reliable coupling.

FIGS. 1 and 2 schematically illustrates the effect of a surface irregularity on an ultrasonic pulse. FIG. 1 shows how the ultrasonic beam on a flat surface is readily focused to the desired area. FIG. 2 shows how the ultrasonic beam is dispersed due to the curved surface. Clearly, if the fidelity of the ultrasonic inspection is to be maintained, variations in the surface profile must be accommodated.

U.S. Patent Application, Publication No. US 2005/0150300, entitled "Device and Method for Ultrasonic Inspection Using Profilometry Data" discloses a method of using several ultrasonic probes on a sled arrangement with water coupling between the transducers and the part surface. The arrangement provides the ability to map out the surface profile in order to correct the inspection of the component by compensating for the error in location of reflectors caused by the uneven surface. However, it does not incorporate the ability to correct the aberration in the ultrasonic beam caused by an uneven surface profile over the width of the ultrasonic beam. Thus, its applicability is restricted to surfaces that can be described as flat over the width of the beam as it enters the surface. This restriction is very limiting since, as seen in FIG. 2, even a 1.5 inch radius of curvature causes severe beam distortion on a typical ultrasonic beam.

A flexible phased array probe has been developed that can be conformed to the surface of complex geometry components to perform ultrasonic inspections. This is described in an article entitled "A Flexible Phased Array Transducer for Contact Examination Of Components with Complex Geometry", presented at the 16th World Conference on Nondestructive Testing in Montreal, Canada Aug. 30-Sep. 3, 2004. In this experimental work, a flexible piezoelectric probe has been developed that has displacement measuring devices attached to each individual element. The individual elements are pushed down to conform to the uneven surface profile. By measuring the vertical position of each individual element with the displacement sensors, phased array delays can be calculated that compensate and eliminate the beam distortion that the irregular surface would otherwise produce. However, maintaining sufficient contact between the probe elements and the part surface to couple the ultrasonics into the part reliably is problematic. To insure good ultrasonic coupling between the elements and the part, a gap of no more than a couple thousandths of an inch filled with a coupling liquid or gel is required. In many practical cases, the surface conditions make this not possible.

An article by C. Holmes, B. Drinkwater, and P. Wilcox, Insight, Vol. 46, No. 11, 677-680 (2004) discloses the use of monolithic (single element) ultrasonic transducers. The ultrasonic beam characteristics are set and cannot be changed. One probe operates with a water path to measure the surface profile and a different probe for the internal inspection is in contact with the surface of the component. Since the ultrasonic probes described in this reference are not flexible, they can only operate on flat surfaces. The flat surface of the probe must be in contact with a flat surface of the component over the entire area of the probe, with a thin liquid couplant between the probe and the component surface not more than a couple of thousandths of an inch thick in order for it to operate properly. Therefore, this device can only work on components that are comprised of flat surface segments. Over the transition regions from one flat area to another, the internal inspection probe cannot operate. This approach can only accommodate curved surfaces that have such a large radius of curvature that they are essentially flat over the area of the probe. For typical transducers, the radius of curvature must be greater than a couple of feet in order to use this approach. The correction provided by this approach is limited to correcting the location of an internal reflection from the ultrasonic data for the variations in the surface profile. Since the beam angle and distance to the reflector from each probe is known and by knowing the exact location of the probe on the surface and the surface profile, the location of the reflector relative to a global coordinate system can be calculated with the approach described in this article. However, the approach is applicable only to a relatively small subset of the uneven surface components that exist. This approach does not address at all the problem of beam distortion that is caused by a surface that is not flat over the area of the probe. This emphasizes that this approach is only applicable to segments of a surface that are flat over the area of the probe.

SUMMARY OF INVENTION

The present invention addresses the deficiencies in the known art and is drawn to a method for ultrasonically inspecting components with wavy or uneven surfaces. A multi-element array ultrasonic transducer is operated with a substantial fluid layer, such as water at least several ultrasonic wavelengths thick, between the array transducer and the component surface. This fluid layer may be maintained by immersing the component in liquid or by using a captive couplant column between the probe and the component surface. The component is scanned, measuring the two dimensional surface profile using a mechanical stylus, laser, or ultrasonic technique. Once an accurate surface profile of the component's surface has been obtained, data processing parameters are calculated for processing the ultrasonic signals reflected from the interior of the component.

The various features of novelty which characterize the invention are pointed out with particularity in the claims annexed to and forming part of this disclosure. For a better understanding of the present invention, and the operating advantages attained by its use, reference is made to the accompanying drawings and descriptive matter, forming a part of this disclosure, in which a preferred embodiment of the invention is illustrated.

BRIEF DESCRIPTION OF THE DRAWINGS

In the accompanying drawings, forming a part of this specification, and in which reference numerals shown in the drawings designate like or corresponding parts throughout the same.

DESCRIPTION OF THE PREFERRED EMBODIMENTS

Figure 1:
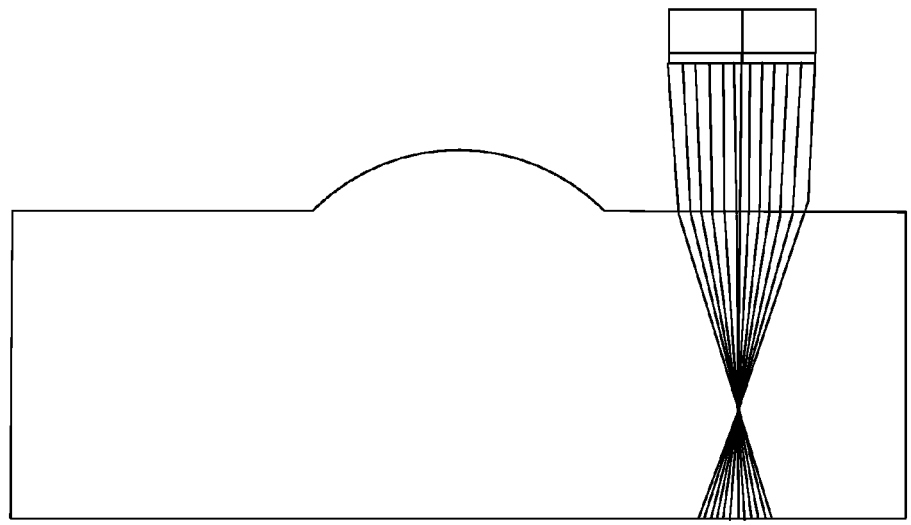
FIG. 1 schematically illustrates the effect of ultrasonic pulses directed into a part through a flat surface.
Figure 2:
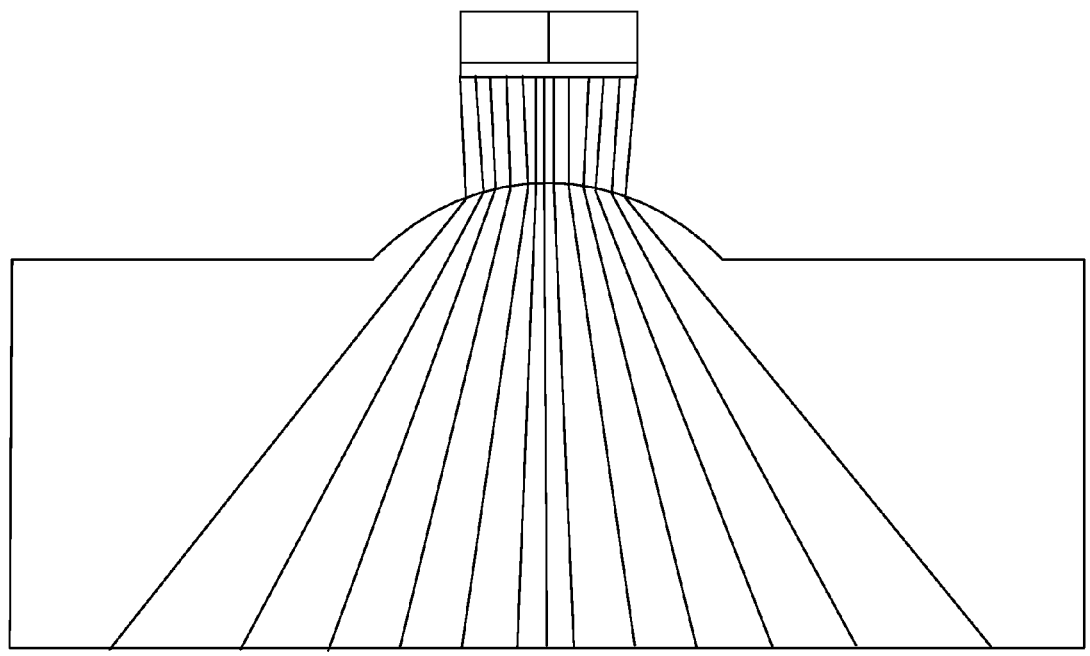
FIG. 2 schematically illustrates the effect of ultrasonic pulses directed into a part through an uneven surface.

While the inventive inspection method may be accomplished in at least three different ways, there are some common areas to each method.

The first common area is that it is preferable to use a multi-element array ultrasonic probe.

Another common area is that the probe is separated from the component to be inspected by a substantial fluid path. The fluid may be water or a gel, but is preferably water as this is easiest to work with. Current ultrasonic transducer inspections are typically carried out in a manner wherein the transducer is coupled to the component being inspected by a fluid or gel that is less than a few thousandths of an inch thick, which means that the transducer is essentially almost touching the component. Thus, for the purposes of the invention, a substantial fluid path is intended to be at least several ultrasonic wavelengths between the transducer and component such that there is a space between the transducer and component that allows a relatively small radius of curvature of uneven surface on the component without resulting in contact between the transducer and component. This water path typically ranges from 3 mm to 25 mm in length.

Another common area is that the component is scanned to obtain a two dimensional surface profile of the component. However, the scanning means used may be different and these will be discussed below.

Another common area is that, based on the measured surface profile of the component, signal processing parameters are calculated as a function of the ultrasonic probe position that correct for ultrasonic beam distortion that would otherwise result from the reflected ultrasonic pulses.

In the preferred embodiment, the component to be inspected is scanned by firing each individual UT probe element in a multi-element array ultrasonic probe one at a time and recording the received reflected ultrasonic waveform from each of the elements in the array so that a complete data set is recorded at each probe position for every unique combination of transmitter element and receiving element. The collected array of ultrasonic waveform data is processed to measure the surface profile of the component. Based on the measured surface profile, signal processing parameters are calculated as a function of probe position that correct for the uneven surfaces and eliminate beam distortion effects that would otherwise occur in the reflected signals from the internal reflectors in the component. The collected array of data is processed, changing the signal processing parameters as a function of encoded probe position calculated in the preceding step to analyze (inspect) the interior of the component based on the reflected signals from the interior of the component.

In the preferred embodiment, the well known Synthetic Aperture Focusing Technique (SAFT) may be used to form the two dimensional aperture required for volumetric point focusing, thereby increasing sensitivity and improving resolution. The SAFT technique is easily applied to the Matrix Firing/Focusing scheme since all of the waveforms from the individual elements are saved. It is then simply a matter of using the waveforms from multiple probe positions in focusing to a single focal point to achieve the SAFT benefits.

In another embodiment, the component to be inspected is scanned to measure the two dimensional surface profile as a function of the encoded probe position using either a mechanical stylus, laser based technique, ultrasonic technique, or similar technique. Based on the measured surface profile, signal processing parameters are calculated as a function of probe position. These signal processing parameters correct for the uneven surfaces to eliminate beam distortion effects that would otherwise occur in the reflected signals. The calculated signal processing parameters are then downloaded into a commercially available phased array instrument that is connected to a two-dimensional ultrasonic array transducer. The component is then scanned with the multi-element array ultrasonic probe using the signal processing parameters downloaded to the phased array instrument to inspect the interior of the component. This is accomplished by electronically selecting the signal processing parameters based on the ultrasonic array probe position and using them to receive, process, and record the pulses that are reflected back from the reflectors in the interior of the component.

In another embodiment, the component to be inspected is scanned as described above to measure the surface profile. At the same time that the component is scanned to measure the surface profile, the multi-element ultrasonic probe array has each individual array element fired one at a time. The received ultrasonic waveform from each of the elements in the array is recorded so that a complete data set is recorded at each probe position for every unique combination of transmitter element and receiving element. The signal processing parameters are calculated based on the measured surface profile as indicated above. The collected array of data received from the individual firing of each element is then processed using the newly calculated signal processing parameters that correct for the surface irregularities and eliminate the beam distortion effects that would otherwise occur in the reflected signals from the interior reflectors in the component.

Each embodiment may be accomplished wherein a single array probe acts as both a transmitter and receiver or two multi-element array probes may be used where one probe acts as a transmitter and the second probe acts as the receiver. Using dual probes as separate transmitters and receivers reduces the amplitude of the reflection from the interface between the fluid and the surface of the component which temporarily "blinds" the system to near-surface reflections from the interior of the component. The operation and calculation of the signal processing parameters using dual probes is the same as when using a single combined transmitter/receiver probe except that the relative location of the two probes is taken into account. In this case the surface profile information is obtained by operating the transmitter probe in pulse/echo mode (transmitting and receiving on the same elements in this probe) at the same time the separate receiver probe is receiving the reflected ultrasound from the interior of the component. The two probes are separated laterally. The transmitter (first) probe transmits ultrasonic pulses into the coupling liquid and interior of the component and receives the ultrasonic reflections from the surface of the component for mapping the surface profile of the component. The receiver, second, probe receives ultrasonic reflections from the interior of the component.

Using the inventive method of acquiring and processing the data, it is possible to process the data to create an image that is the equivalent of having an ultrasonic beam focused at each point in the region of interest. It is also possible to process the data from different numbers of elements for different regions of the component, effectively varying the aperture. For example, the effective aperture can be increased with increased focal distance to maintain a constant focal width for the inspected area since the focal width is given by:

Focal Width~=(Focal Distance)(Ultrasound Wavelength)/(Effective Probe Width)

The general means in which the inventive method is accomplished is discussed below.

The surface profile of a component can be accurately measured using array probe ultrasonics. This is accomplished by scanning over the component part while electronically sweeping the beam in angle, collecting ultrasonic surface reflection data, and then combining the collected data using the known beam angle and position of the probe when the data was taken to create an accurate profile of the part's surface. The largest reflection from a point on the surface is obtained when the ultrasonic beam is perpendicular to the surface. When combining the data for each beam angle and position of the probe, the reflection with the highest amplitude from a given point on the surface is used to measure the distance from the probe to the point on the surface. Knowing the precise location of the probe and beam angle for the largest reflection, the location of the point on the surface can be determined. The entire surface can be profiled by performing this measurement for a grid of points to define the surface. Signal processing that is equivalent to the phased array processing that is described above can be performed for the Matrix Firing collected data to provide the same surface profiling capability.

To profile an entire surface, an ultrasonic beam is swept in angle while scanning over the part. When properly gated, the resultant signals give information on the amplitude and time of arrival of the peak signal for each beam angle at each probe location. The spatial location of the source of the reflection, relative to the probe, can be calculated from this information as follows:

$$x = \frac{ToF \cdot v_s}{2} \sin\theta$$

$$y = \frac{ToF \cdot v_s}{2} \cos\theta$$

Here ToF is the measured time of flight for the reflection, $V_s$ is the velocity of sound in the liquid, and $\theta$ is the angle of the focused beam. These relative position values are added to the known probe position when the reflection was recorded to provide the actual x, y location of the reflector and stored in an array. The profile of the part is found by processing the array as a function of x position to find the y location of the reflection with the maximum amplitude for each x position. By repeating this process with multiple scan lines taken at increments along the length of the component the entire surface profile for the component can be generated.

Figure 3:
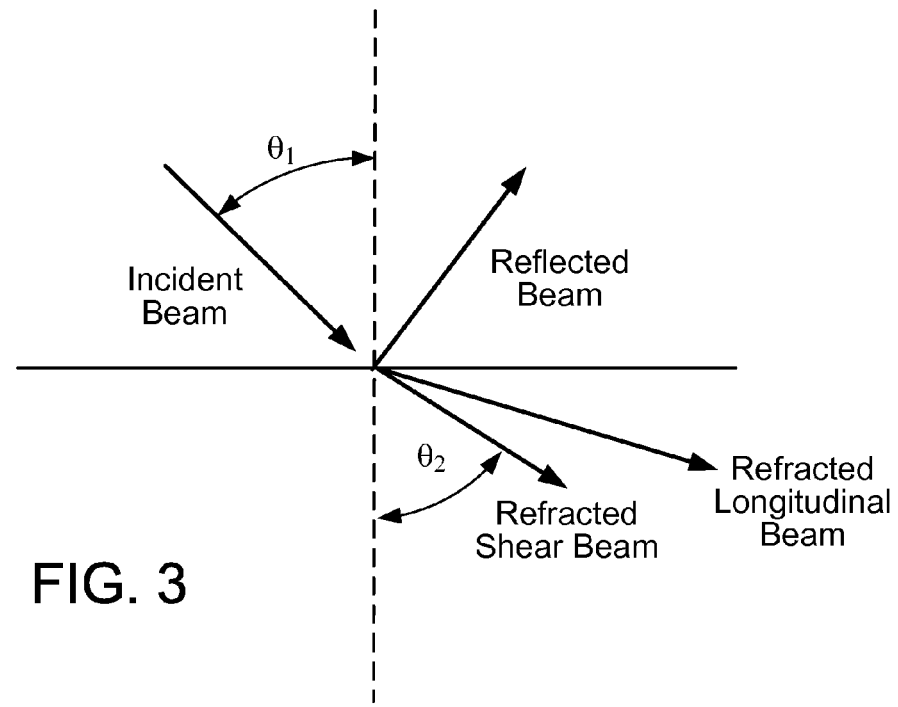
FIG. 3 schematically illustrates ultrasonic beam refraction and reflection at the interface of two different materials.

In order to accurately calculate the time delay values used for processing the data from the interior of the component, the path taken by the ultrasound in traveling from a transducer element to a point of interest in the component must be determined. An ultrasonic wave propagating from the source element through the liquid/solid interface at the component surface refracts at the interface. FIG. 3 illustrates this refraction. An incident ultrasonic wave strikes the surface at an angle of $\theta_1$. The wave is refracted at the interface and travels in the component at an angle $\theta_2$ given by Snell's Law:

$\theta_2 = \sin^{-1}(V_2 \sin(\theta_1)/V_1)$ $\theta_1$=incident angle in first material (liquid)
$\theta_2$=refracted angle in second material (solid component)
$V_1$=sound velocity in first material (liquid)
$V_2$=sound velocity in second material (solid component)

$V_2$ can be either the shear wave velocity or the longitudinal velocity of the solid resulting in either a shear wave beam or a refracted longitudinal wave beam. Calculating the time delays to use for inspecting a component with an uneven surface requires finding the refracted path between the source element and the desired focal point that passes through the uneven surface at a point that satisfies Snell's Law. Typically this is done via numerical root finding. An error function can be defined that goes to zero when a path is found from the center of an individual element, through a point in the uneven surface, to the desired focal point that satisfies Snell's Law. This error function is given by:

$$E(x) = X_{focus} - Y_{focus} \tan(\sin^{-1}(V_2 \sin(\theta_1)/V_1))$$

$X_{focus}$ is the horizontal distance from where the incident ray intersects with the surface to the desired focal pointing X, $Y_{focus}$ is the depth below the surface where the incident ray intersects the surface to the desired focal point, $\theta_1$ is the incident angle relative to the surface normal, $V_1$ is the ultrasonic velocity of the coupling liquid, and $V_2$ is the ultrasonic velocity of the solid component. The error function is evaluated as a function of x along the part surface. When a value for x is found that such that E(x) is equal to zero within some predetermined tolerance, a solution for the sound path that satisfies Snell's Law has been found and the beam passes through the surface at this x value. Other methods of finding solutions that satisfy Snell's Law can also be used. Once the ultrasound path solution is found, a straightforward calculation provides the time of flight for a signal to travel along this path from which the signal processing delays can be calculated.

$$\text{ToF} = (\text{Path Length in Liquid})/V_{liquid} + (\text{Path Length in Solid})/V_{solid}$$

Figure 4:
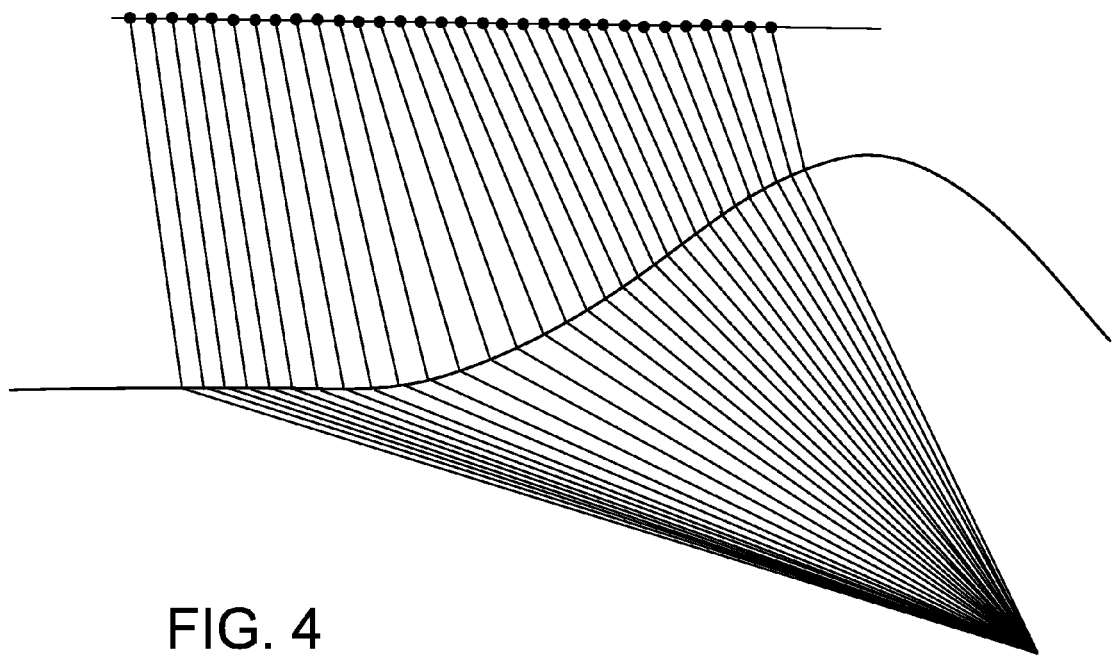
FIG. 4 is an example of the raytracing for a multi-element array probe.

In FIG. 4 an example of the raytracing for a multi-element (32) array probe operating through a complex geometry surface is shown. The material above the interface is water and the material below the interface is steel.

This approach can be extended to three dimensions when using a 2D array probe. A 2D array probe typically contains a rectangular two dimensional array of elements. With these probes, focusing through an uneven surface involves solving for the ultrasonic path in all three dimensions x, y, and z.

The invention provides several advantages.

Figure 5:
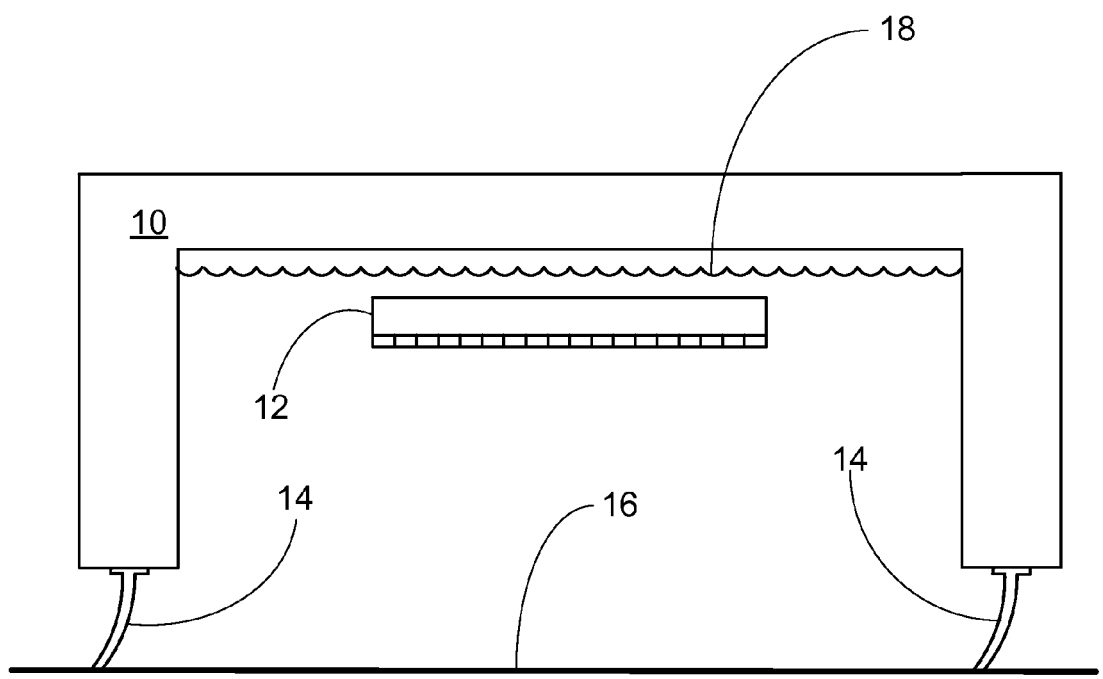
FIG. 5 illustrates the use of a captive couplant column between the ultrasonic probe and component surface.

One of the primary advantages is that by using a water path between the part and the probe, a simple array probe can be used and scanned over the part surface with relative ease in order to perform the inspection. The water path can be provided by immersing the component in a tank of liquid to perform the inspection. As seen in FIG. 5, a water path can also be established by using a small container 10 around the probe 12 with a flexible seal 14 against the surface of the component 16 and injecting a liquid 18 into the container 10 to fill the region between the probe surface and the part surface. Although a brush type seal 14 is shown, it should be understood that any suitable seal, such as a rubber gasket, may be used. The use of the coupling liquid generally provides reliable coupling and lends itself to automatic scanning. The water path also provides a convenient means for measuring the surface profile of the part as described above.

Figure 6:
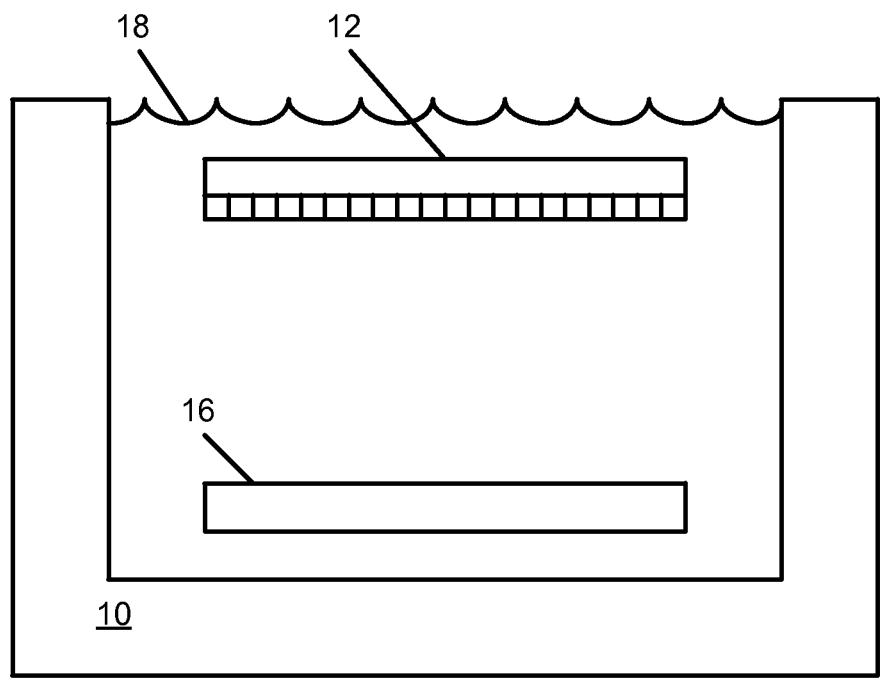
FIG. 6 illustrates an embodiment where the component to be inspected is immersed along with the ultrasonic probe.

Turning to FIG. 6, FIG. 6 illustrates an embodiment according to the present invention where container 10 is designed to hold a sufficient volume of a liquid 18 (e.g., water, or some other liquid) so that both component 16, as well as, probe 12 can be immersed therein. As would be apparent to those of skill in the art, although FIG. 6 illustrates the embodiment where probe 12 is located closer to the surface of liquid 18, such positioning is not critical to this embodiment and the reverse orientation is also within the scope of the present invention. That is, where component 16 is located closer to the surface of liquid 18 and probe 12 is located closer to the bottom of container 10.

Another advantage of the invention is that it allows the elimination of ultrasonic beam distortion for the inspection as well as accurately locating reflectors in the interior of the component. As illustrated earlier, even relatively small deviations from a flat surface can cause severe distortion of an ultrasonic beam passing through the surface. It can be shown that this approach is quite robust for a wide range of uneven surface conditions, including a step in the surface. Because of this advantage, this technique can address a wide range of uneven surface inspection problems.

For the implementation of this technique utilizing matrix firing and matrix focusing in which the ultrasonic waveforms from every unique combination of transmitting and receiving element is digitized and saved for later processing, it is possible to determine the surface profile and perform an inspection of the interior of the component with the same data or alternately with separate data simultaneously acquired from one raster scan over the surface of the component. This is advantageous because it eliminates the need to perform two scans to separately obtain the surface profile data and interior of the component inspection data. In addition, the surface profile must be measured very accurately to be able to accurately correct the ultrasonic beam for the uneven surface. By using the same data or simultaneously obtaining the surface profile and interior inspection data, it is assured that the two measurements are acquired at precisely the same locations of the probe. The accurate measurement of the surface profile to within a few thousandths of an inch or less is possible with this approach. This allows distortion due to the uneven surface to be eliminated and provides for very accurate location of the reflectors within the interior of the component.

The invention makes it possible to employ advanced signal processing techniques that are not possible with commercially available phased array instruments. In particular, it is possible to process the data to provide an image that has been focused at every point in the inspection region, providing improved image resolution. In addition, it is possible to vary the effective aperture (width) of the inspection probe to provide a constant focal width and, therefore, resolution throughout the inspection region. Since the "raw" data can be saved, the data can be reprocessed at any time with any number of different focusing parameters to provide additional information to better characterize the reflector. This improved characterization could be extremely advantageous where the repair or replacement of a component determined to have a significant defect is very costly.

Another advantage is the ability to use very simple hardware to acquire the data. For example, the best implementation envisioned is to use an array of simple pulser circuits and an array of simple receiver circuits connected to high speed digitizers all working in parallel to digitize the received waveforms and transfer them to a computer for processing. There would be very few parameters needed to be defined to operate this hardware. In contrast, commercially available phased array hardware contains, in addition to the pulser/receivers and digitizers described above, devices for providing programmable rapid switched electronic delays for both the transmit pulse and the received signals. They also contain circuitry for summing the delayed signals from each of the receiver channels. All of this requires a large number of parameters to be programmed in order for it to operate.

Another advantage is the ability to also employ Synthetic Aperture Focusing Technique (SAFT) to augment the inspection provided from the active elements used to acquire data from a fixed location of the probe. With SAFT, data in the waveforms collected from the individual elements, from multiple positions of the probe, are summed together after an appropriate delay is applied to the data. This is essentially the same processing as is used for Matrix Focusing except that the data for SAFT comes from multiple precisely known positions of the probe. With Matrix Focusing, data taken from every unique combination of transmitter and receiver element is used in the processing and can be shown to be equivalent to the processing performed in commercially available phased array instruments in so far as the resulting waveform is concerned. With SAFT, the data is collected over a larger area, resulting in a larger effective aperture providing improved resolution and sensitivity than for the data collected at a single location of the probe. However, since the data is only collected for the physical elements of the probe, the SAFT processed data is not the exact equivalent to having a larger area active probe. SAFT can be very effective in improving the resolution and sensitivity of the inspection.

The use of a full 2D array probe with small enough elements and sufficient quantity of elements to provide good beam characteristics when operating on 2D varying surfaces can be problematic. Transducers with larger numbers of 2D elements are difficult to build, expensive, and have poor sensitivity if the elements become too small. The amount of time it takes to fire, collect, and process the data from a large number of elements could be prohibitive for the matrix firing approach. Hardware for supporting large numbers of elements (>32) is not readily available. One approach that avoids the use of large numbers of elements in a 2D probe is the use of the Synthetic Aperture Focusing Technique (SAFT) to provide one dimension of the required two dimensional array of waveform data sets. With SAFT, a 1D array probe with narrow lateral width can be fabricated to provide good beam spread for an individual element in the lateral direction. The 1D array probe is raster scanned over the surface of the part, collecting the data as described for the Matrix Focusing approach. The data is then processed using a combination of Matrix Focusing and SAFT. This has the practical advantage of very straightforward hardware implementation. Although it can be shown that in some cases this does not provide as good sensitivity as a full 2D array, it can be a very practical approach to the inspection of components that have surfaces that vary in two dimensions. SAFT can be used to augment the processing of the data collected in either direction or both directions.

While specific embodiments and/or details of the invention have been shown and described above to illustrate the application of the principles of the invention, it is understood that this invention may be embodied as more fully described in the claims, or as otherwise known by those skilled in the art (including any and all equivalents), without departing from such principles.

What is claimed as invention is:

1. A method for ultrasonically inspecting components with uneven surfaces, comprising:
   a. providing a fluid coupling of at least several ultrasonic wavelengths thick between a probe that contains an ultrasonic transducer and a component by immersing the component in liquid and providing a space between the transducer and component that allows an uneven surface on the component without contact between the transducer and component, the ultrasonic transducer comprising an array of small unfocused elements with each element producing substantial beam spread;
   b. measuring the two dimensional surface profile of the component as a function of encoded ultrasonic probe position, wherein measuring the two dimensional surface profile comprises the steps of:
      (i) scanning the component, firing each individual ultrasonic element one at a time;
      (ii) for each firing, simultaneously recording the received reflected ultrasonic waveform from both the surface and interior reflectors from each element in the array; and
      (iii) processing the collected array of ultrasonic waveform data to sweep an ultrasonic beam in angle at each probe position and, using the known angle and probe position, measure the surface profile of the component;
   c. calculating signal processing parameters based on the measured surface profile, as a function of the encoded ultrasonic probe position, to eliminate ultrasonic beam distortion; and
   d. downloading the calculated signal processing parameters to the ultrasonic instrument, to a processing unit or to a data storage device.

2. The method of claim 1, wherein the two dimensional surface profile of the component is determined using the same ultrasonic transducer instrument used to inspect the interior of the component.

3. The method of claim 1, wherein the ultrasonic instrument used is a multi-element phased array ultrasonic instrument.

4. The method of claim 1, wherein:
   a. first and second multi-element array ultrasonic probes, separated laterally, are used to perform the inspection;
   b. the first ultrasonic probe is used to transmit ultrasonic pulses into the coupling liquid and interior of the component and to receive the ultrasonic reflections from the surface of the component for mapping the surface profile of the component; and
   c. the second ultrasonic probe is used to receive ultrasonic reflections from the interior of the component.

5. A method for ultrasonically inspecting components with uneven surfaces, comprising:
   a. providing a fluid coupling of at least several ultrasonic wavelengths thick between a probe that contains an ultrasonic transducer and a component by immersing the component in liquid and providing a space between the transducer and component that allows an uneven surface on the component without contact between the transducer and component, the ultrasonic transducer comprising an array of small unfocused elements with each element producing substantial beam spread;
   b. measuring the two dimensional surface profile of the component as a function of encoded ultrasonic probe position, wherein measuring the two dimensional surface profile comprises the steps of:
      (i) scanning the component, firing each individual ultrasonic element one at a time;
      (ii) for each firing, simultaneously recording the received reflected ultrasonic waveform from both the surface and interior reflectors from each element in the array; and
      (iii) processing the collected array of ultrasonic waveform data to sweep an ultrasonic beam in angle at each probe position and, using the known angle and probe position, measure the surface profile of the component;
   c. calculating signal processing parameters based on the measured surface profile, as a function of the encoded ultrasonic probe position, to eliminate ultrasonic beam distortion; and
   d. processing the collected array of data from each individual transducer element using the newly calculated signal parameters to correct for surface irregularities in the component.

6. The method of claim 5, wherein:
   a. first and second multi-element array ultrasonic probes, separated laterally, are used to perform the inspection;

b. the first ultrasonic probe is used to transmit ultrasonic pulses into the coupling liquid and interior of the component and to receive the ultrasonic reflections from the surface of the component for mapping the surface profile of the component; and c. the second ultrasonic probe is used to receive ultrasonic reflections from the interior of the component.

7. The method of claim 5, wherein synthetic aperture focusing technique is used during the step of processing the collected array of data.

8. A method for ultrasonically inspecting components with uneven surfaces, comprising:

a. providing a fluid coupling of at least several ultrasonic wavelengths thick between a probe that contains an ultrasonic transducer and a component wherein the fluid coupling is created by a liquid captive couplant column located between the component and the probe so as to allow the inspection of an uneven surface on the component without contact between the transducer and component, the ultrasonic transducer comprising an array of small unfocused elements with each element producing substantial beam spread;

b. measuring the two dimensional surface profile of the component as a function of encoded ultrasonic probe position, wherein measuring the two dimensional surface profile comprises the steps of:
  (i) scanning the component, firing each individual ultrasonic element one at a time;
  (ii) for each firing, simultaneously recording the received reflected ultrasonic waveform from both the surface and interior reflectors from each element in the array; and
  (iii) processing the collected array of ultrasonic waveform data to sweep an ultrasonic beam in angle at each probe position and, using the known angle and probe position, measure the surface profile of the component;

c. calculating signal processing parameters based on the measured surface profile, as a function of the encoded ultrasonic probe position, to eliminate ultrasonic beam distortion; and d. downloading the calculated signal processing parameters to the ultrasonic instrument, to a processing unit or to a data storage device.

9. The method of claim 8, wherein the two dimensional surface profile of the component is determined using the same ultrasonic transducer instrument used to inspect the interior of the component.

10. The method of claim 8, wherein the ultrasonic instrument used is a multi-element phased array ultrasonic instrument.

11. The method of claim 8, wherein:
a. first and second multi-element array ultrasonic probes, separated laterally, are used to perform the inspection;
b. the first ultrasonic probe is used to transmit ultrasonic pulses into the coupling liquid and interior of the component and to receive the ultrasonic reflections from the surface of the component for mapping the surface profile of the component; and
c. the second ultrasonic probe is used to receive ultrasonic reflections from the interior of the component.

12. A method for ultrasonically inspecting components with uneven surfaces, comprising:

a. providing a fluid coupling of at least several ultrasonic wavelengths thick between a probe that contains an ultrasonic transducer and a component wherein the fluid coupling is created by a liquid captive couplant column located between the component and the probe so as to allow the inspection of an uneven surface on the component without contact between the transducer and component, the ultrasonic transducer comprising an array of small unfocused elements with each element producing substantial beam spread;

b. measuring the two dimensional surface profile of the component as a function of encoded ultrasonic probe position, wherein measuring the two dimensional surface profile comprises the steps of:
  (i) scanning the component, firing each individual ultrasonic element one at a time;
  (ii) for each firing, simultaneously recording the received reflected ultrasonic waveform from both the surface and interior reflectors from each element in the array; and
  (iii) processing the collected array of ultrasonic waveform data to sweep an ultrasonic beam in angle at each probe position and, using the known angle and probe position, measure the surface profile of the component;

c. calculating signal processing parameters based on the measured surface profile, as a function of the encoded ultrasonic probe position, to eliminate ultrasonic beam distortion; and d. processing the collected array of data from each individual transducer element using the newly calculated signal parameters to correct for surface irregularities in the component.

13. The method of claim 12, wherein:
a. first and second multi-element array ultrasonic probes, separated laterally, are used to perform the inspection;
b. the first ultrasonic probe is used to transmit ultrasonic pulses into the coupling liquid and interior of the component and to receive the ultrasonic reflections from the surface of the component for mapping the surface profile of the component; and
c. the second ultrasonic probe is used to receive ultrasonic reflections from the interior of the component.

14. The method of claim 12, wherein synthetic aperture focusing technique is used during the step of processing the collected array of data.

* * * * *